(12) United States Patent
Decker

(10) Patent No.: US 7,207,140 B1
(45) Date of Patent: Apr. 24, 2007

(54) VEGETATIVE PLANTING MATERIAL AND METHOD FOR PRODUCING IT, USEFUL IN GRASS SOD PRODUCTION

(75) Inventor: Henry F. Decker, Ostrander, OH (US)

(73) Assignee: Buckeye Bluegrass Farms, Inc., Lewis Center, OH (US)

( * ) Notice: Subject to any disclaimer, the term of this patent is extended or adjusted under 35 U.S.C. 154(b) by 0 days.

(21) Appl. No.: 10/745,516

(22) Filed: Dec. 29, 2003

Related U.S. Application Data

(60) Provisional application No. 60/445,647, filed on Feb. 6, 2003.

(51) Int. Cl.
  *A01B 79/00* (2006.01)
  *A01B 79/02* (2006.01)
  *A01C 1/00* (2006.01)
  *A01G 1/00* (2006.01)
  *A01H 3/00* (2006.01)

(52) U.S. Cl. .............. 47/58.1 SE; 47/DIG. 1; 111/200; 111/900; 111/919

(58) Field of Classification Search ......... 111/200, 111/900, 915, 917–919; 47/1.01 R, 58.1, 47/77, DIG. 1, 58.1 R, 58.1 SE
See application file for complete search history.

(56) References Cited

U.S. PATENT DOCUMENTS

| | | |
|---|---|---|
| 4,986,026 A | 1/1991 | Decker |
| 5,177,898 A | 1/1993 | Decker |
| 5,481,827 A | 1/1996 | Decker |
| 5,806,445 A | 9/1998 | Decker |
| 5,899,020 A | 5/1999 | Decker |
| 5,998,700 A * | 12/1999 | Lightfoot et al. ........... 800/278 |
| 6,123,036 A | 9/2000 | Decker |
| 6,223,662 B1 | 5/2001 | Lastinger et al. |
| 6,286,253 B1 | 9/2001 | Decker |

OTHER PUBLICATIONS

Beard, JB, "Turfgrass: Science and Culture," (1973), relevant portions of Chapters 3 and 4.
Brede, D., "Turfgrass Maintenance Reduction Handbook: Sports, Lawns, and Golf," (2000), relevant portions of Chapters 2 and 5.
Decker, H., "Producing Sods over Plastic in Soilless Media," Horticul. Rev., V. 27: 317-351 (2001).
Decker, HF, et al, "Lawn Care A Handbook for Professionals," (1988), pp. 48-52, 254-257.

* cited by examiner

*Primary Examiner*—Christopher J. Novosad
(74) *Attorney, Agent, or Firm*—Susan Petraglia

(57) ABSTRACT

The invention provides a new form of vegetative propagating material, referred to as "the grass plantlet", as well as a method for producing it. The new vegetative planting material and the method by which it is obtained make it possible to replicate and increase both warm and cool season grasses more rapidly than by the conventional methods of seeding, sprigging, or plugging. Three to five new, clean, and pure generations of a newly developed seeded or vegetative cultivar can be obtained each year. Outcrossing, the need for burning and possibly for herbicide use are eliminated by the present invention. The present methodology embodies a sterile production system resulting in grass plantlets that are free of nematodes, pathogenic fungi, and damaging insects. The method of the invention has the capacity to rapidly reproduce and to maintain the genetic purity of promising new cultivars that would otherwise be discarded because they are sterile hybrids, low seed producers, sterile direct DNA transfers, or cross pollinated non-apomicts.

21 Claims, No Drawings

VEGETATIVE PLANTING MATERIAL AND METHOD FOR PRODUCING IT, USEFUL IN GRASS SOD PRODUCTION

CROSS-REFERENCE TO RELATED APPLICATION

The present invention is based on provisional patent application Ser. No. 60/445,647, filed on Feb. 6, 2003, the entire contents of which are herein incorporated by reference.

FEDERAL FUNDING LEGEND

This invention was produced in part using funds obtained through grant CREES Award No. 2001-33610-11058 from the Small Business Innovative Research (SBIR) program of the U.S. Department of Agriculture. Consequently, the federal government has certain rights in this invention.

FIELD OF THE INVENTION

The invention provides a new grass vegetative propagating material, a method for producing it, and their application to improved methods of new cultivar replication that are made more time-efficient, genetically-controlled, and cost-effective as compared to prior art methods and planting materials.

BACKGROUND OF THE INVENTION

In earlier experiments, the present inventor studied vegetative propagation on a field scale in several southern warm season turfgrasses, particularly the bermudagrasses. Many warm season grasses are sterile hybrids and do not set seed, or set enough seed, to be propagated economically by seed. Hence, many of these grasses are reproduced vegetatively by "sprigging." Sprigs are a material harvested from verticutting mature fields of sod, or obtained from shredding bulk sod of the grass as, e.g., in Lastinger et al U.S. Pat. No. 6,223,662. Alternatively, these warm season grasses may be reproduced vegetatively by "plugging", i.e., planting what are typically three-inch square pieces of grass sod into soil.

Another method of propagating grasses other than by "sprigging", "plugging" or seeding was disclosed in the present inventor's earlier issued patents U.S. Pat. Nos. 5,899,020, 5,806,445, and 6,286,253. In the system described in those patents, whole pieces of sod of the cultivar to be propagated are separated into pieces of vegetative planting material (or VPM). Sod used for VPM production is typically grown over plastic sheeting or any root-impervious surface, making it possible to reduce soil contamination from nematodes, deleterious insects, and pathogenic micro-organisms, and also to maintain the integrity of the primary rooting system. VPM is produced over plastic sheeting from "whole sods" which are comprised of complete root systems, stems, stolons, rhizomes, ramets, crowns, culms, leaves, and all. Sods grown over plastic sheeting can also be harvested much earlier than sods grown directly on soil as indicated in my earlier patents. Being able to harvest sods for VPM production much quicker is a very distinct advantage in the production of this new type of vegetative propagating material.

In the methods of the earlier patents mentioned above, sods were separated into vegetative pieces by shredding or milling whole pieces of mature harvested sod. I discovered that this method of separation destroyed too much meristematic tissue, diminishing the quantity and vigor of viable vegetative planting material. Accordingly, in an effort to improve upon this earlier method of separation, I discovered a much less damaging method of producing vegetative planting material which, consequently, improved significantly the yield or quantity of viable vegetative planting material obtained. Concomitantly, I discovered: (a) an entirely new form of vegetative propagating material which I have named Grass Plantlets; (b) a method for producing them; and (c) a new methodology for the rapid replication of newly planted cultivars. These and other aspects of the invention are described in more detail below.

SUMMARY OF THE INVENTION

The main object of the invention is to disclose the discovery of a new form of vegetative planting material, hereinafter referred to as "grass plantlets", and to provide a method of producing grass plantlets.

Another object of the invention is to provide a method of producing grass plantlets, wherein the method includes improved separation means that contribute to obtaining a higher percentage of intact and active meristems in the harvested grass plantlets resulting in a very high quality planting material for plant replication.

A further object of the invention is a methodology that enables the practitioner to obtain grass plantlets in significantly high yields while working with immature or juvenile sods that are less than 3 months old.

It is a further object of the invention to provide a method of maintaining the genetic purity of a new, selected, or desired cultivar throughout development and production over subsequent generations.

It is yet a further object of the invention to provide a method for greatly increasing the rate of replication of a new cultivar throughout development and production to obtain in a lesser number of years over conventional practices, mature grass sods that are ready to produce a seed or sod crop. More particularly, according to the present invention three to six new, clean, genetically pure generations of a new seeded cultivar can be obtained each year, as compared to obtaining only one generation per year by seed propagation methods.

Further still the invention provides a method for propagating and maintaining the genetic purity of cultivars that would otherwise be discarded because of, e.g., sterility, low seed production, or loss of desirable genotype in non-apomictic varieties due to cross-pollination in a seed field. Additionally, the present methodology enables the rapid expansion of the availability, on a field scale, of planting materials of sterile transgenic hybrids.

These and other improvements accomplished by the present invention will become further evident in the following detailed disclosure.

DESCRIPTION OF THE INVENTION

The new vegetative propagating material of the invention, "Grass Planlets", comprise young, active, typically small pieces of meristematic tissue that can be harvested and separated with complete roots, stems, and leaves from young sods (less than 3 months old) grown over plastic sheeting. Sprigs, in comparison, are produced by verticutting mature sods grown directly in soil or by shredding off-site mature (over 9 months old) soil-grown sods after harvest in which the primary roots are cut off. Another difference between grass plantlets and sprigs is that the former are typically much smaller and more dense per bushel than are sprigs.

Grass Plantlets are harvested from whole young sods with intact root systems and leaf tissue already germinated and growing. They are also harvested directly in the field which makes it possible to produce this new and refined vegetative propagating material more rapidly and, in view of the simultaneous recycling of the growing medium at the field site, more economically. The inventor feels that a very important advantage of the invention is that since grass plantlets are grown from young sods that have a much quicker crop turnover than sprigs, an equal amount of effective growing material can be produced on much less acreage. Further still, when freshly planted, using methods described in our earlier patents, grass plantlets are more evenly and densely spread and have the capacity to establish sods and playing surfaces more quickly than by plugging, sprigging, or even seeding. Hence, grass plantlet technology foreseeably will replace the conventional practices of sprigging, plugging, seeding and possibly even sodding with many grasses.

Grass plantlets are best compared to grass seedlings (see TABLE I). An important distinction is that grass plantlets are in the asexual line of plant development, while grass seedlings are in the sexual line (and hence replication is subject to outcrossing and, consequently, loss of genetic purity of the particular cultivar being replicated.) Thus, when replicated vegetatively, a new cultivar should remain genetically pure over many replications using grass plantlets and the associated methodology. Grass plantlets have the capacity to develop more rapidly since they are already comprised of mature tissues complete with roots, stems, and leaves and with the capacity to form secondary tissues such as tillers, rhizomes, and stolons, which are very important in the production of a sod. Grass seedlings, however, must first go through a germination period, often several weeks, and then a development period before they are comparable in maturity to grass plantlets.

TABLE I

| GRASS SEEDLING | GRASS PLANTLET |
| --- | --- |
| sexual in origin | asexual in origin |
| comprised of primary (immature) tissues | comprised of secondary (mature) tissues |
| has to germinate and mature before ready to produce secondary tisuues (tillers, stolons, and rhizomes) | already mature, growing and producing secondary tissues (tillers, stolons, and rhizomes) |
| requires planting, watering, and diligent care | requires planting, watering, and diligent care |
| produces only one generation per year | can produce several generations per year |
| genetically mixed | genetically pure |
| replication is subject to outcrossing | replication eliminates outcrossing |

Using grass plantlets and grass plantlet methodology, 3 to 6 new, clean, genetically pure, generations of a new seeded cultivar can be obtained each year compared to only one generation per year by seed propagation methods. Accordingly, this represents a significant advance in the art of seed production. Frequently, it takes five to ten (5–10) years to grow enough new cultivar seed to plant fields large enough to make harvesting the new seed profitable. During this long period of development, or "bulking up", seed growers must constantly contend with the reality of outcrossing that attends seed field propagation. The advance brought by the present invention "bulks up" the large fields in a fraction of the time, as well as maintains the genetic purity of the new cultivar during that time frame. Hence, a seed producer using grass plantlets and grass plantlet methodology can conceivably be in full seed production in only a year or two, instead of the typical five to ten or more years using conventional practices.

By using grass plantlets it is often possible to rapidly replicate a grass cultivar. For example, harvestable sods of the turfgrass Sea Isle paspalum can be produced in just 4–5 weeks over plastic with impressive yields of grass plantlets of over 100 (defined as, or meaning that, 1 square foot of a young Sea Isle sod will produce enough grass plantlets in 4 to 5 weeks to plant 100 square feet of new sod). In contrast, it was an interesting observation made by the inventor during the developmental phases of the present invention that older, more mature sods grown in soil in the conventional manner have very poor yields of grass plantlets, with decreased vegetative vigor. Hence, starting with a mere ten-acre nursery of a grass as prolific as Sea Isle paspalum, the method of the invention and the new vegetative planting material described herein make it possible to produce enough grass plantlets to plant 800 acres of new sod every 4–5 weeks during the growing season. Further still, with 4 to 5 crop turnovers in a growing season, one could expect to produce from the original ten-acre nursery several thousand acres of sod every year, by using grass plantlets and the methodology associated therewith. The same techniques can be used to rapidly replicate bermudagrasses, Zoysias, and other warm season grasses in 5 to 8 weeks.

In additional research surrounding the present invention (supported by the USDA grant referenced above) and dealing particularly with vegetative propagation, the study was extended to include northern cool season grasses, such as bentgrass and bluegrass. Many cool season grasses are prolific seed producers and hence are commercially propagated from seed rather than by vegetative propagation. Nevertheless, several of these grasses can spread vegetatively with impressive vigor, often as quickly as some of the warm season bermudagrasses. Accordingly, the technique of the present invention also enables the rapid replication of bentgrasses and bluegrasses and other cool season grasses in approximately 10 to 12 weeks. Thus, from just a square foot of breeder stock or from a few grams of seed, ten-acre nurseries of, e.g., bentgrass or bermudagrass can be quickly established and capable of producing enough vegetative planting material to plant 500 to 700 new acres of sod every 10–12 weeks.

It was also discovered that both cool and warm season turfgrass cultivars can often be produced, propagated, and increased more rapidly by using the subject grass plantlets than by seeding, sprigging, or plugging. Moreover, the amount of grass plantlets required to produce a warm season bermudagrass or a cool season bentgrass sod was observed by the inventor to be approximately the same. Hence, from just a square foot of sod or a few grams of seed of a new cultivar, the present method can produce enough planting material of the new cultivar to have in just 1 to 2 years hundreds of acres of mature grass ready to produce a seed or sod crop. The present invention significantly speeds up the development time and production time for both vegetative and seeded new cultivars.

In TABLE II that follows the first column (A) shows various cool and warm season grasses used to exemplify the invention. At the top of the list are two cool season grasses, bentgrass and bluegrass. Column B indicates the number of grass plantlets planted in each instance. For example, in a typical planting according to the invention but on an experimental scale, 50 grass plantlets were mixed in a liquid slurry consisting of water, wood fiber, fertilizer, and other amendments. The plantlet-containing slurry was then spread evenly over plastic sheeting. When the liquid mulch had slightly dried, it was covered with 0.25 to 0.50 inches of a selected, functionally axenic, growing medium or combinations of growing media.

TABLE II

| A<br>Source of<br>vegetative<br>planting<br>material | B | C | | | D | Y |
|---|---|---|---|---|---|---|
| | | Jun. 2, 2001 | Jul. 2, 2001 | Aug. 2, 2001 | | |
| Bentgrass | 50 | 50 | 100 | 100 | 8 | 57[1] |
| Bluegrass | 50 | 40 | 85 | 90 | 8 | 20 |
| Buffalograss | 50 | 30 | 50 | 80 | 14 | 14 |
| Zoysiagrass | 50 | 20 | 60 | 95 | 12 | 14 |
| Centipede | 60 | 30 | 60 | 80 | 12 | 14 |
| St. Augustine | 35 | 30 | 80 | 100 | 8 | 7 |
| Bermuda | 70 | 50 | 100 | 100 | 8 | 48 |

A: Grass vegetative planting material according to the invention
B: number of grass plantlets planted per square foot
C: after the initial planting on May 2, "C" designates the percent cover at 4, 8, and 12 weeks
D: designates the week from initial planting during which the sod could be lifted and harvested
Y: yield = area (in sq. ft.) that one square foot of sod grown from grass plantlets will plant
[1] a mature, one year old, conventional soil-grown bentgrass sod, when separated using the same means of separation provided for by the invention, had a yield of only 28.

The plantings in TABLE II were made on May 2, 2001. By June 2 (4 weeks) the bentgrass covered about 50% of the plastic sheeting, while bluegrass covered about 40% (see Col. C). At 8 weeks (July 2) the bentgrass showed 100% cover and would now hold together well enough to be harvested as a sod. Bluegrass showed only 85% cover, but its root system was so well-developed at 8 weeks that it, too, was easily harvested as a sod (Col. D). The result and discovery is as follows: a cultivar does not have to have a complete cover in order to be harvested for its grass plantlets.

Another unexpected discovery and advantage of the present method arose out of the experiments summarized in Table II. Focusing for the sake of example on the cool season bentgrass, the yield shown in Column Y is 57. This means that one square foot of an 8 week-old sod grown from grass plantlets could be separated into enough new (second generation) grass plantlets to plant 57 new square feet at the original planting rate of 50 grass plantlets/square foot. One would assume that an original, tight, mature (1 year old), soil-grown conventional bentgrass sod ready for harvest and for planting on a golf green would have a yield considerably greater than a sod that is only 8 weeks old and grown over plastic. To the contrary, the opposite was observed: the older conventional sod had a yield of only 28, compared to the 8 week-old sod in which the yield was 57. The inventor interprets these results as both an important discovery and advance to the art and concludes the following from the observed result: as grass sods become tighter, more dense, and more mature, their vegetative vigor, as well as the vigor of vegetative planting material derived therefrom, is substantially decreased. This is circumvented by growing the sod over plastic sheeting for a period of, e.g., 8 weeks, yielding a harvestable sod with greater vegetative vigor.

Although not as dramatic as the result for bentgrass, the same was true of bluegrass which produced more grass plantlets from an 8 week-old sod grown from grass plantlets over plastic than was obtained from a one year old, soil grown, mature sod ready for conventional harvesting.

As for the warm season grasses shown in TABLE II, the following should be noted about their test performance. This experimental series was conducted in Ohio where the springs are typically cold and warm season grasses, such as St. Augustinegrass, Zoysiagrass and others, are sluggish until mid-summer. In theory and in practice in the indigenous climate of these grasses, one would expect to see a higher percentage of cover more rapidly from the time of initial planting and higher yield values when practicing the present invention.

Thus in a broad embodiment of the invention, a method is provided for the production of grass plantlets as a new form of vegetative propagating material. These new grass plantlets are useful in the rapid cultivation of both seeded and vegetative grass cultivars. The method comprises a) harvesting from the growing surface of a locus a juvenile sod together with growing medium in which the sod was growing, b) employing gentle separating means to separate the juvenile sod into a vegetative fraction apart from the growing medium, without damage to meristematic tissue of the vegetative fraction, c) further separating the vegetative fraction obtained by subjecting it to either the same gentle separating means used in step b) or other suitable gentle separating means provided that such means do not damage meristematic tissue of the vegetative fraction, to isolate small complete grass plantlets comprised of root, stem, and leaf tissue; and d) recycling the growing medium separated in b) by returning it to the growing surface of the locus to be used in subsequent rounds of generating more grass plantlets and ultimately sods grown therefrom. All of the above recited steps are conducted directly at the growing locus. The "locus" can be an outdoor setting (e.g. a field) or an indoor green/fieldhouse setting. The "growing surface" of the locus is intended, in a preferred embodiment of the invention, to mean a surface other than the natural soil surface of a field or of the earth in general. For example, a substantially root-impervious surface such as a cement abandoned parking lot or air strip could be used for raising young sods in growing media and harvesting grass plantlets therefrom in the appropriate number of weeks. More preferably, due to the important objectives of growing sods in sterile media for the rapid replication of cultivars that are free from nematodes, insects, and pathogenic microorganisms, and for providing a novel planting material similarly "clean" to achieve that objective, the growing surface is preferably a sheet substrate that is laid down on top of, e.g., a dirt field surface. In this preferred embodiment, the sheet substrate is a plastic sheeting that has been laid down in advance of growing the first sod. The method of the invention can also be practiced on sods that are conventionally soil-grown. However, it has been observed that the yield of the resulting grass plantlets are considerably lower when compared to those obtained from sods grown over plastic sheeting, and hence this is a less preferred embodiment of the invention.

Hence, grass plantlets are harvested from selected young sods that are less than 3 months old which are grown, preferably, over plastic sheeting. Typically, it has been observed that for warm season grass varieties young sods of about 5 to about 10 weeks in age and cool season grasses from about 10 to 12 weeks old are harvestable. The technique of growing sod over plastic sheeting traps the primary rooting system which forms a sod much more quickly than in the conventional process of growing sod on soil which relies largely on secondary rooting (tillers, stolons, and rhizomes) to effect a sod usually in 9 months or more. Young sods in the grass plantlet process are cut, lifted and harvested using a proprietary mobile apparatus having means for accomplishing the cutting and lifting operations and further comprising the gentle separation means over which the cut and lifted young sod is conveyed. The gentle separation means comprises one or more pin cylinder(s) to which are attached carefully-sized, shaped, and specially-positioned 1 to 3-inch hard pins. Alternatively, one or more wire-wound metallic cloth cylinders that gently separate the sod into small, complete, active, plantlets, may be used in place of the pin cylinder(s). It is further envisioned that a combination of pin cylinder(s) and wire-wound metallic cloth cylinder(s) can be used to accomplish the gentle and effective separation of young sods into grass plantlets.

In the current process young sods are gently separated into a vegetative fraction, apart from the growing medium (which is returned to the planting surface to be used again for a subsequent crop), that is separated out with much less tissue damage than observed by using hammermills or shredders as proposed in my earlier patents, and by Lastinger et al in U.S. Pat. No. 6,223,662. The vegetative propagating material that is produced comprises grass plantlets already growing with functioning roots, stems, and leaves. These small grass plantlets are an excellent material for replicating new cultivars. Once through the initial gentle separation, the harvested, separated, grass plantlets may be subjected to an additional separating step using means to remove any remaining growing medium. The "other gentle separation means" that may be employed in the present method to effect additional separation of the vegetative fraction from the growing medium have no particular limitation save for the requirement that whatever is utilized must not destroy the vital meristematic tissue of the vegetative fraction. Accordingly, with the knowledge gleaned from the prior art techniques of shredding and milling, namely that these means destroy too much vital plant tissue, shredding and milling means would not be suitable as the other gentle separating means. However for the sake of example, a mechanism that effects physical vibration or agitating treatments (e.g., a fan, or a wet (water) agitation treatment when the initially separated grass plantlets are transferred to a hydroplanter) are within the purview of the invention as "other gentle separation means". For example, the harvested, separated, grass plantlets can be made to travel over a series of mat chain, open conveyors, which may be part of the same apparatus that incorporates the gentle separation means and which series of mat chain, open conveyors is subsequent to the step of initial gentle separation, in order to vibrate off any remaining growing medium. The clean grass plantlets are then conveyed into a trailing forage wagon for processing off-field (for example, such processing includes, but is not limited to, washing, rinsing with sterilants, and bagging) either for replanting or for shipment to markets.

In the case of replanting, the harvested and processed grass plantlets are spread evenly over a planting surface in a manner described in U.S. Pat. Nos. 5,806,445 and 6,123,036 (the contents of which are herein incorporated by reference) at the rate of about 50 to 100 plantlets per square foot which is much more dense than when planting sprigs or plugs. The grass plantlets are spread very evenly with a minimum of overlap and exposed to intense and unobstructed sunlight which greatly speeds the spreading process and, hence, sod formation when compared to seeding, sprigging, and especially when compared to plugging. Again, for warm season varieties, young workable sods are obtained in approximately 5–10 weeks, and for cool season varieties, 10–12 weeks. In a preferred embodiment, since sods are grown over plastic sheeting in sterile growing media, the growing sod is protected from nematodes, insects, and pathogenic micro-organisms. Since the process yields a planting material that is sterile and free of any deleterious organisms, and further is easy to ship and quick to grow, new U.S. cultivars grown according to the invention should be readily acceptable in overseas markets. Moreover, if intended for replanting at some time in the future since the grass plantlets are complete little plants, they store much better than vegetative planting material obtained by shredding or milling. If refrigerated, grass plantlets can be stored for several months or shipped in air freight containers at 6–7° C.

A very important contribution that the present invention makes to the art and the commercial field is in providing a method and planting material by which genetic purity can be controlled or maintained in cultivars. Since grass plantlets are replicated asexually, genetic purity can be maintained (selected or "fixed") in grasses where the genetics are not fixed by apomixis (i.e., an otherwise sexually-replicating grass). Also, grass plantlet technology makes possible the fixing of genetic purity in crosses where it is also possible to fix heterosis.

The present innovation can also rapidly expand in one to two years the availability on a field scale of planting materials of direct, but sterile, DNA transfers (a.k.a. a sterile transgenic hybrid). Thus a method is provided for rapidly expanding the availability on a field scale of planting material of a sterile transgenic hybrid grass cultivar by taking a first generation sterile transgenic hybrid cultivar grown in a suitable growing medium on a growing surface (natural or artificial) and subjecting it to the methods described above for generating grass plantlets to obtain grass plantlets therefrom. Next, replanting the grass plantlets so obtained in the growing medium recycled from the first generation harvest, and growing the grass plantlets for a time sufficient for grow-in and sod formation (5–10 weeks in age for warm season grasses, 10–12 weeks in age for cool season grasses). Then subjecting the $2^{nd}$, $3^{rd}$, $4^{th}$, . . . $n^{th}$ generation young sods to the method of generating grass plantlets and replanting subsequent generations of planting material for a necessary number ("n") of replications (or rounds) to obtain increased quantities of the cultivar sufficient to plant on a field scale. "n" is defined as a positive integer.

According to the present invention, it takes approximately from about 1 to about 2 years to accomplish this rapid expansion of planting material to arrive at field scale quantities, as compared to 5 to 10 years for conventional "bulking up" practices.

The invention further provides methodology for rapidly reproducing and maintaining the purity of promising new cultivars that would otherwise be discarded because they are sterile, low seed producers, or cross pollinated non-apomicts.

Thus the invention provides a method for maintaining genetic purity of a new cultivar throughout development and production over subsequent generations, comprising obtaining grass plantlets for a given cultivar as previously described in the method of producing grass plantlets, planting the grass plantlets in a growing medium on a planting surface for a time sufficient for grow-in and sod formation of 5–10 weeks in age for warm season grasses or 10–12 weeks in age for cool season grasses, and repeating the cycle of growing young sods and harvesting grass plantlets therefrom for a desired number of replications to obtain further generations of planting material of the cultivar, wherein the genetic purity of the further generations can be maintained relative to the parent stock.

Since the present method and planting material eliminate the occurrence of outcrossing in conventional seed field propagation, the genetic purity of new seeded cultivars can be maintained over successive generations. Moreover, since the grass plantlets are grown vegetatively and harvested from young sods grown over plastic sheeting and sterile growing media, and further replanted under the same sterile and protective environment, the invention advantageously substantially if not totally eliminates the need for the undesirable practice of field burning and reduces the need for herbicides, which are necessary to control weeds and undesired offtypes in conventional seed field propagation.

The foregoing description and examples point in a direction indicative of the great potential of the present methodology and new planting material. Namely, that grass plantlet technology foreseeably will replace the conventional practices of sprigging, plugging, and even sodding with many grasses. It is also within the scope of the invention that the methods herein described and claimed have applications that reach beyond turfgrass applications. The present advancement of the art can, without undue experimentation, be applied to other plant groups such as grass and legume forage crops (e.g., alfalfa), grasses harvested for their fruit (e.g., grain crops such as rice, wheat, barley, corn), ornamental grasses, and grasses that are grown for fuel such as Distichlis and others. It is further envisioned that the present methods of generating a new vegetative planting material and using such material in impressively faster replication of a desired cultivar over conventional propagation methods will extend to the areas of monocot and dicot food and horticultural crops, without resort to undue experimentation.

While the invention has been specifically illustrated and described in connection with numerous embodiments and further defined in the appended claims, modifications to the various embodiments are within the spirit and scope of the present invention and will be readily apparent to those of skill in the art.

I claim:

1. A method of producing grass plantlets as a vegetative propagating material useful in the replication and cultivation of both seeded and vegetative grass cultivars, comprising:
   a. harvesting, from a locus having a natural or artificial growing surface thereon, a juvenile sod less than or equal to three months old together with growing medium in which the sod was growing;
   b. physically separating as a first separation step, said juvenile sod into a vegetative fraction and a growing medium fraction without damage to meristematic tissue of said vegetative fraction;
   c. separating further, as a second separation step, said vegetative fraction obtained in step b) to isolate grass plantlets, each plantlet comprised of root, stem, and leaf tissue and without damage to meristematic tissue; and
   d. recycling said growing medium separated in step b) by returning said growing medium to the locus having said growing surface thereon, said growing medium to be reused in subsequent rounds of producing more grass plantlets and sods grown therefrom, wherein steps a)–d) are conducted directly at the locus having said growing surface thereon.

2. The method according to claim 1 wherein said harvesting comprises removing said juvenile sod from a sheet substrate growing surface.

3. The method according to claim 2, wherein said harvesting comprises cutting and lifting said juvenile sod off of a plastic sheeting growing surface.

4. The method according to claim 1, wherein said first separation step is accomplished using at least one of a) a pin roller, and b) a metallic clothe cylinder.

5. The method according to claim 4, wherein said second separation step is accomplished using at least one of a) a pin roller, and b) a metallic clothe cylinder.

6. Grass plantlets produced according to the method of claim 4.

7. The method according to claim 1 further comprising, after step d), a step e) planting grass plantlets obtained in step c) in said recycled growing medium to produce a subsequent generation of grass plantlets.

8. The method according to claim 1 wherein harvesting occurs between 5 and 10 weeks of age for a warm season grass sod.

9. The method according to claim 1 wherein harvesting occurs between 10 and 12 weeks of age for a cool season grass sod.

10. Grass plantlets produced according to the method of claim 1.

11. A method for maintaining genetic purity of a first generation cultivar throughout development and production over subsequent generations, comprising
   a. obtaining grass plantlets of a first generation cultivar by growing, harvesting and physically separating a sod in accordance with the method of claim 1;
   b. planting the grass plantlets in a growing medium on a planting surface, and growing said plantlets for a time to reach grow-in and sod formation, wherein said time for grow in and sod formation is from about 5–10 weeks for warm season grasses or from about 10–12 weeks for cool season grasses;
   c. obtaining next generation grass plantlets from sod formed in step b) in accordance with harvesting and first and second separating steps of the method of claim 1;
   d. planting the grass plantlets obtained in step c) in a growing medium on a planting surface, and growing said plantlets for a time to reach grow-in and sod formation, wherein said time for grow in and sod formation is from about 5–10 weeks for warm season grasses or from about 10–12 weeks for cool season grasses;
   e. repeating steps c) and d) to obtain further generations of plantlet planting material of said cultivar, wherein genetic purity of said further generations is maintained.

12. A grass cultivar having a fixed genotype from first generation throughout development and production over subsequent generations, produced according to the method of claim 11.

13. A seeded or vegetative grass cultivar having a fixed genotype from first generation throughout development and production over subsequent generations, produced according to the method of claim 11.

14. A grass cultivar having a fixed genotype from first generation throughout development and production over subsequent generations produced according to the method of claim 11, wherein said cultivar is non-apomictic.

15. A grass cultivar having a fixed genotype from first generation throughout development and production over subsequent generations produced according to the method of claim 11, wherein said first generation of said cultivar is genotypically an occurrence of heterosis.

16. A sterile grass cultivar having a fixed genotype from first generation throughout development and production over subsequent generations produced according to the method of claim 11.

17. A low seed-producing grass cultivar having a fixed genotype from first generation throughout development and production over subsequent generations produced according to the method of claim 11.

18. A method for expanding the availability on a field scale of planting material of a sterile transgenic hybrid grass cultivar, comprising
 a. obtaining grass plantlets from a first generation sterile transgenic hybrid grass cultivar in a first round of grass plantlet production by growing, harvesting and physically separating a sod of a first generation sterile transgenic hybrid grass in accordance with the method of claim 1;
 b. planting grass plantlets obtained in step a) if performing a second round of grass plantlet production, or planting grass plantlets obtained in step c) if performing a third or subsequent round of grass plantlet production, in a growing medium on a planting surface and growing for a time to reach grow-in and sod formation, said time is approximately from 5–10 weeks for warm season grasses or approximately 10–12 weeks for cool season grasses;
 c. obtaining next generation grass plantlets from the sod formed in step b) by harvesting and physically separating said sod in accordance with the method of claim 1; and
 d. repeating steps b) and c) for n number of replications, wherein n is a positive integer and n replications result in obtaining further generations and increased availability of planting material of said sterile transgenic hybrid cultivar sufficient to plant on a field scale.

19. The method according to claim 18, further comprising practicing steps a–d for a duration of from about one year to about two years to obtain expanded availability of planting material sufficient for field scale planting.

20. A grass plantlet of a cultivar consisting essentially of a grass vegetative planting material having intact root, stem, and leaf tissue, and undamaged meristematic tissue, wherein said plantlet has a genetic purity that is maintained from a first generation plantlet throughout development and production over subsequent generations of plantlets.

21. A grass plantlet according to claim 20, which is of a cultivar or variety selected from the group consisting of a vegetative new or first generation cultivar, a seeded new or first generation cultivar, a cool-season grass, a warm-season grass, a naturally-sterile cultivar, a cultivar having sterility induced by direct DNA transfer, a low-seed producing cultivar, and a non-apomict cultivar at risk of loss of desirable genotype by seed field cross-pollination.

* * * * *